United States Patent [19]

Lavie

[11] Patent Number: 5,280,791
[45] Date of Patent: Jan. 25, 1994

[54] MONITOR SYSTEM FOR DETERMINING THE SLEEP STAGES OF A PERSON

[75] Inventor: Peretz Lavie, Danya, Israel

[73] Assignee: The Sleep Disorders Diagnostic And Treatment Center, Ltd., Israel

[21] Appl. No.: 963,057

[22] Filed: Oct. 19, 1992

[30] Foreign Application Priority Data

Nov. 19, 1991 [IL] Israel .................................. 100080

[51] Int. Cl.$^5$ ............................................ A61B 5/0402
[52] U.S. Cl. .................................... 128/696; 128/708
[58] Field of Search ................ 128/696, 708; 340/575

[56] References Cited

U.S. PATENT DOCUMENTS 4,784,162 11/1988 Ricks et al. ........................ 128/903
4,836,219 6/1989 Hobson et al. ..................... 128/782

OTHER PUBLICATIONS

1: "Ethology of Sleep Studied with Time-Lapse Photography: Postural Immobility and Sleep-Cycle Phase in Humans," J. Allan Hobson, et al., Science, vol. 201, Sep. 29, 1978, pp. 1251-1253.

Primary Examiner—William E. Kamm
Assistant Examiner—Scott M. Getzow
Attorney, Agent, or Firm—Morgan & Finnegan

[57] ABSTRACT

A simple system for determining a non-invasive sleep state of a person is described. The system comprises: (a) means for measuring the person's cardiac R-R waves interval; (b) means for calculating the power spectrum of the cardiac R-R interval, thus obtaining a ratio between spectral power in the and high frequencies; (c) means responsive to the measuring and calculating means for generating output signals, one output signal having a first value when said ratio is above a specific predetermined threshold, designated as REM sleep-and one outputs signal having a second value when the above ratio is below this threshold, designated as non-REM sleep, and (d) means responsive to the output signal for designating a time period of predetermined duration as a REM period or a non-REM period, respectively. The system enables an accurate determination of the sleep state.

10 Claims, 2 Drawing Sheets

MONITOR SYSTEM FOR DETERMINING THE SLEEP STAGES OF A PERSON

The present invention relates to sleep monitors. More particularly, the invention relates to a sleep monitor system for determining a non-invasive sleep state, which differentiate between various stages of sleep and wakeful states.

BACKGROUND OF THE INVENTION

Normal individuals experience several distinct sleep states. One important sleep state is characterized by Rapid Eye Movement, known as REM sleep, small muscle twitches, changes in autonomic activity and the absence of other body movements. The other sleep state, known as Non-REM (NREM) sleep is subdivided into four stages, wherein the first stage is the most shallow, i.e., the least restful or refreshing, and the fourth stage is the deepest.

Monitoring an individual's sleep is very important for diagnosing sleep disorders. It also is useful in various fields, such as therapy, diagnosing and following response to treatment of depression and narcolepsy in which REM latency is significantly reduced, or in research.

For diagnosis, the patient's sleep stages should be monitored to determine the pattern and duration of various sleep stages. Sleep is qualitatively and quantitatively evaluated by measuring electrical signals produced by brain and muscle activity, using electrophysiological technique and electronic instruments.

A widely used technique for this purpose, involves a simultaneous and continuous measuring of electroencephaographic (EEG) data. EEG data are signals derived primarily from the cortex of the brain and also are referred to as electrocortigram (ECoG). At the same time an electromyogram (EMG) signal which monitors muscle activity, generally from one of the muscles of the lower jaw is measured, together with left eye and right eye electro-oculogram (EOG) signals produced by eye movements. These EEG, EMG and EOG signals are conventionally recorded on a multichannel physiological recorder.

Photographic techniques also have been used to evaluate sleep state. According to Hobson et al.(Science 201,1978, p.1251-5), the mobility of sleeping subjects is measured photographically and the predicted transitions between NREM and REM are done on the premises that major body posture shifts occur immediately preceeding and following REM sleep.

According to U.S. Pat. No. 4,784,162, an apparatus is described for monitoring sleep disorders using a plurality of sensors adapted for attachment to a patient. The sensors generate analog signals which are subsequently converted to binary data to be transmitted by low-power radio. According to U.S. Pat. No. 4,836,219, a method and device are described for reporting an individual's sleep state using electronic filters applied to analog signals representative of eye movements and head movements from detectors attached to a headgear.

Among the main disadvantages of the above methods, there can be mentioned the following:

A high rate of false positive REM detections, by providing a signal indicating the occurrence of REM sleep, when no REM sleep actually is involved. The reason is that the eye movement detector also indicates pick gross body movements which are not part of the typical changes in REM sleep.

The robust construction of the various components as well as the costly equipment and skilled labour required for the interpretation of the results obtained.

In view of the difficulties with existing sleep evaluation techniques, there are many cases, where sleep disorders are not tested with the above known techniques and are treated with sedative-hypnotic drugs without a prior detailed sleep evaluation.

It is an object of the present invention to provide a simple and inexpensive system to determine a non-invasive sleep state. It is another object of the present invention to provide a simple system to determine an accurate non-invasive sleep state. It is yet another object of the present invention, to provide a system for determining a non-invasive sleep state, which does not require skilled personnel.

DESCRIPTION OF THE INVENTION

The invention relates to a system for determining the sleep state of a person, which comprises: (a) means for measuring the person's cardiac R-R waves interval; (b) means for calculating the power spectrum of the cardiac R-R interval, thus obtaining a ratio between spectral power in slow and high frequencies; (c) means responsive to the measuring and the calculating means for generating output signals one output signal having a first value when, designated as REM sleep, and one output signal having a second value when the above ratio is below this threshold, designated as NREM sleep, and (d) means responsive to the output signal for designating a time period of predetermined duration as a REM period or a non-REM period respectively. The preferred spectral power is generally in the range of between 0.01 to 0.07 Hz for the slow frequency and between 0.2 to 0.3 Hz for the high frequency.

DETAILED DESCRIPTION OF THE INVENTION

According to a most preferred embodiment, suggested for a more accurate determination of the sleep state, the system includes means responsive to the person's body movements for generating a second analog signal and means responsive to the second analog signal for designating periods of substantial body movements as wake periods. In order to differentiate between the wake, REM and NREM states, the body-movement detector is connected to means responsive to the second analog signal. This signal does generate a second output signal which has-a first value during a body movement and a second value during the absence of the body's movement.

The system also includes means to designate predetermined periods as body-movement or non body-movement periods, responsive to the second output signal. An electronic signal representative of a sleep state, is produced responsive to both the first and second output signals. The electronic signal is obtained by using electronic storage means for providing reference signals representative of criteria for designating sleep state and means for comparing those reference signals to the first and to the second output signal values.

The system according to the present invention is particularly useful for a simple and inexpensive determination of a non-invasive sleep state. ECG electrodes combined with a miniature body movement sensor are attached to the chest, so there is no need for any additional equipment or electrical attachment to the individual. Today, the techniques for ambulatory monitoring of ECG is quite developed and widely used in cardiology. Monitoring by ECG does not inconvenience patients and allow them to sleep without any interruptions.

An advantage of the invention is the unobstructive automatic sleep state indicator, which does not require subjective operator evaluation and does not involve EEG, EMG or EOG measurements.

DETAILED DESCRIPTION OF THE FIGURES

Figure 1:
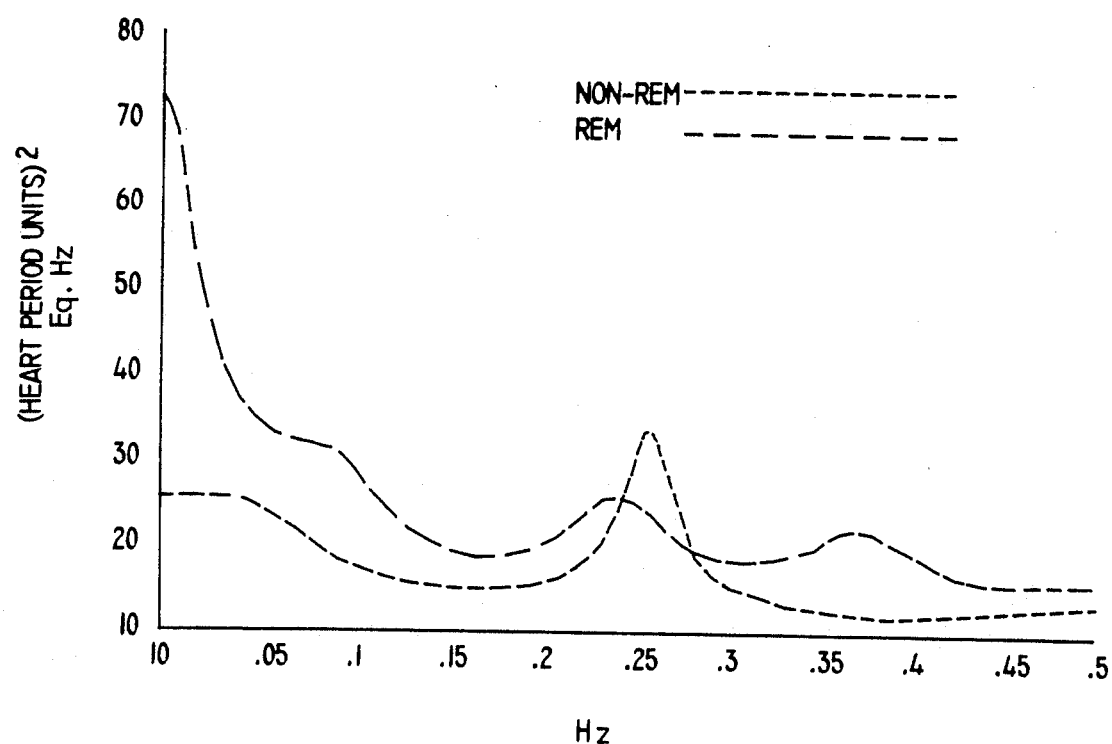
FIG. 1, is a graph which correlates the spectral power as a function of frequency, in case of REM and NREM states of an individual.

FIG. 1 presents the differential distribution of spectral power in REM and NON-REM sleep of an individual. There is a clear peak at 0.25 Herz in a NON-REM and a prominent spectral peak at the slowest frequency in REM sleep. The values of the NON-REM peak at the fast frequencies are much higher than the corresponding REM values.

Figure 2:
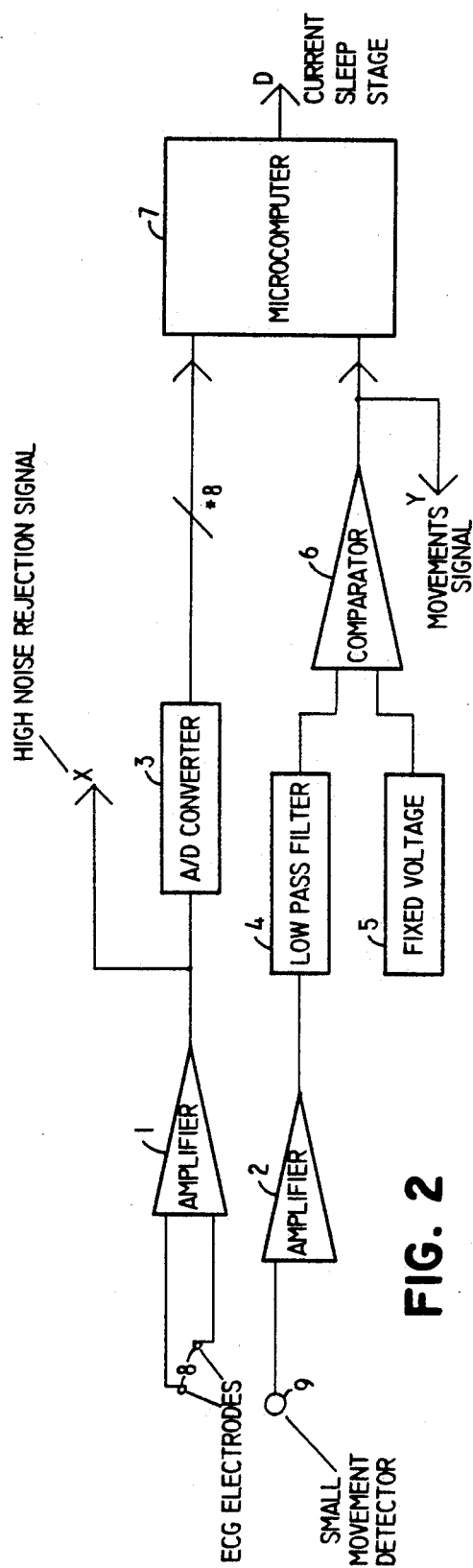
FIG. 2, is a schematic illustration view of a system for reporting a person's sleep state.

In FIG. 2, the system is illustrated by the sleep state wherein the imputs apparatus are connected to two ECG electrodes (8) and to a small movement detector (9), such as a piezo film accelerometer. The small microvolts signals from the ECG electrodes are amplified and filtered by an amplifier suitable for biological signals (i) which possesses a very high impedance and a tailored frequency response to achieve high noise rejection signal (X). The output from the movement sensor is also amplified by its dedicated amplifier (2) and is conveyed after filtering in a low pass filter (4) to a comparator (6). The comparator circuit compares the amplified and filtered signal from the accelerometer to a fixed, predetermined voltage (5), producing a digital signal which indicates the presence or absence of movements signal (Y). The ECG signal obtained from the amplifier and the digital movement signal, are conveyed to a dedicated microcomputer (7) as imputs.

The ECG signal is conveyed by an eight bit A/D converter (3) in the microcomputer circuit to a stream of bytes which act as imput to a real time peak detector It was found that the sampling of the imput should be at least 30 Herz, i.e. 30 samples per second, in order to minimize noise from sample jitter. The time between the peaks, designated as the R-R interval, is stored in a vector serving as input to a real time FFT (Fast Fourier Transform) algorithm. The desired output of the program corresponds to the relative amplitudes at frequency bands in the range of 0.01–0.07 and 0.2–0.3 Hertz, and the R-R times are calculated at an approximate rate of 1 per second, i.e., as is the heart rate of a sleeping person. In order to obtain a reliable resolution, at least 10 samples per cycle are required with the algorithm performing a 10 point FFT, producing amplitudes every 0.05 Hz. In case that a more exact frequency resolution is needed, then a longer input vector can be used. The output from the FFT routine is used together with the data resulting from the movement detector, in order to establish the current sleep stage (D). The above components of the apparatus can be implemented in a very small box, to be located just near the person, or even fixed on his body together with the corresponding batteries.

Figure 3:
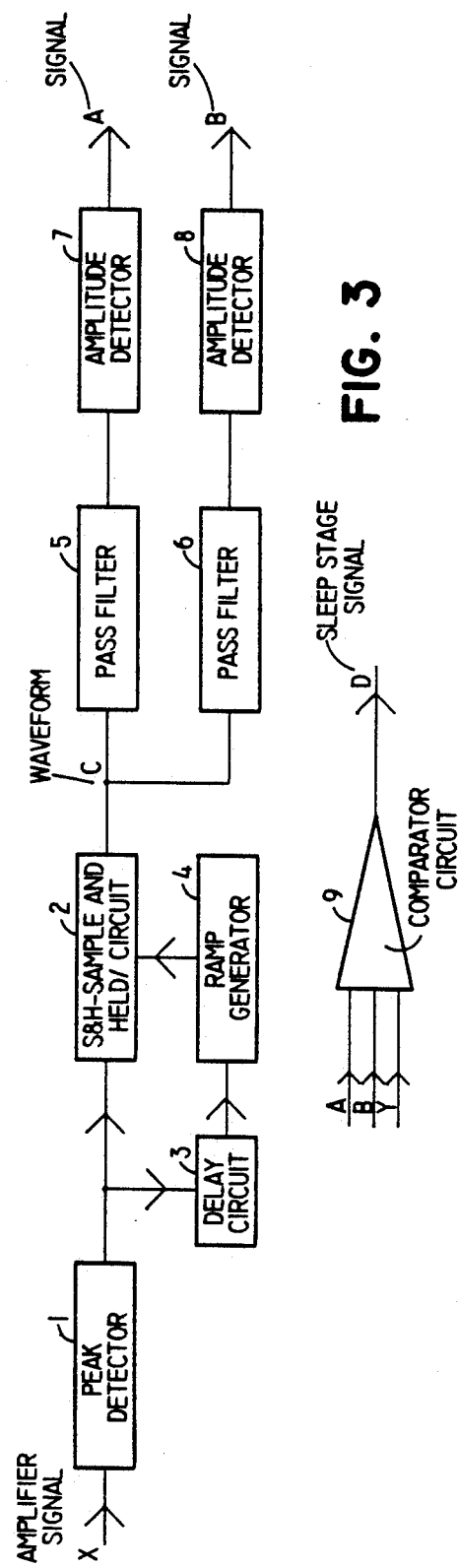
FIG. 3, is a schematic diagram of the electronic circuit used in the system of FIG. 2.

FIG. 3, illustrates an alternative approach to the problem based on a circuit. Shown therein are a peak detector (1), a ramp generator (4), a S&H-Sample and Held-circuit (2) and 2 pass filters (5, 8). The peak detector (1) sends a pulse at every peak of the input waveform from the amplifier/filter, as received from amplifier—signal X—in FIG. 2. At each pulse, the S&H (2) samples the ramp voltage and then the ramp is reset to zero after a delay, by the delay circuit (3), and the cycle starts again. In this manner, a waveform (signal C) is generated having an amplitude relative to the R-R interval. This waveform is filtered by two Band Pass Filters (BPF- 5,6) corresponding to the two frequency bands of interest, and subsequently their amplitudes are extracted by two amplitude detectors (7,8) thus producing the signals A and B. The signals are compared with each other in the comparator circuit (9), with the input from the movement detector serving as a gate, to establish the sleep stage (signal D).

Although the invention has been described only in respect to some embodiments, it should be understood that many changes, or replacements of some items of the apparatus with other parts which can fulfil the same purpose, may be inserted without being outside from the scope of the invention as covered by the appended Claims.

I claim:

1. A system for determining the sleep status of a person, which comprises:
   (a) means to measure the person's cardiac R-R waves interval;
   (b) means to calculate the power spectrum of the cardiac R-R interval, including means for calculating a ratio between spectral power in the slow and high frequencies;
   (c) means responsive to said measuring and calculating means for generating output signals, one output signal having a first valve when said ratio is above a specific predetermined threshold, designated as REM sleep, and one output signal having a second value when the above ratio is below this threshold, designated as non-REM sleep; and
   (d) means responsive to the output signals for designating a time period of predetermined duration as a REM period or a non-REM period, respectively.

2. The system for determining the sleep state of a person according to claim 1, wherein said spectral power is in the range of between 0.01 to 0.07 Hz for the slow frequency and between 0.2 to 0.3 Hz for the high frequency.

3. The system according to claim 1, comprising means responsive to the second value of the output signal to designate periods of body movements as wake periods.

4. The system according to claim 3, including means to designate predetermined periods as body-movement or non body-movement periods responsive to the output signals having said first and second values.

5. The system according to claim 3, wherein said first and second values of said output signals are obtained by an electronic measuring device.

6. The system according to claim 5, further including electronic storage means, wherein said electronic signal is obtained by using said electronic storage means for comparing stored reference signals to the first and to the second output signal values.

7. The system according to claim 5 further including two Band Pass Filters and wherein the second output signal values generate a waveform having an amplitude relative to the R-R interval, which is filtered by two Band Pass Filters.

8. The system according to claim 7 further including two detectors and a comparator circuit, wherein the amplitudes obtained are extracted by said two detectors thus generating two signals which are compared in a comparator circuit.

9. The system according to claim 1, wherein said means for measuring a person's cardiac R-R waves interval comprises cardiac electrodes and a miniature body movement sensor and the cardiac R-R electrodes combined with the miniature body movement sensor are adapted to be attached to the chest of a person.

10. The system according to claim 9, wherein said movement sensor is a piezo film accelerometer.

* * * * *